US008686733B2

(12) United States Patent
Brucker (10) Patent No.: US 8,686,733 B2
(45) Date of Patent: Apr. 1, 2014

(54) IONIZATION GAUGE HAVING ELECTRON MULTIPLIER COLD EMISSION SOURCE (75) Inventor: Gerardo A. Brucker, Longmont, CO (US)

(73) Assignee: Brooks Automation, Inc., Chelmsford, MA (US)

( * ) Notice: Subject to any disclaimer, the term of this patent is extended or adjusted under 35 U.S.C. 154(b) by 705 days.

(21) Appl. No.: 12/808,983

(22) PCT Filed: Dec. 17, 2008

(86) PCT No.: PCT/US2008/013790
§ 371 (c)(1),
(2), (4) Date: Oct. 20, 2010

(87) PCT Pub. No.: WO2009/085165
PCT Pub. Date: Jul. 9, 2009

(65) Prior Publication Data
US 2011/0234233 A1 Sep. 29, 2011

Related U.S. Application Data (60) Provisional application No. 61/008,185, filed on Dec. 19, 2007.

(51) Int. Cl.
*G01L 21/30* (2006.01)
(52) U.S. Cl.
USPC .................. 324/460; 315/533; 315/105 CM; 324/464; 250/283
(58) Field of Classification Search
USPC .......................................................... 324/460
See application file for complete search history.

(56) References Cited

U.S. PATENT DOCUMENTS 4,270,091 A 5/1981 Mann
4,298,817 A 11/1981 Carette et al.
(Continued)

FOREIGN PATENT DOCUMENTS

CN 1834288 A 9/2006
DE 4137527 A1 5/1993
(Continued)

OTHER PUBLICATIONS

Notification of Transmittal of the International Search Report and the Written Opinion of the International Searching Authority, or the Declaration, PCT/US2008/013790, 14 pp., mailed Jul. 31, 2009.
(Continued)

Primary Examiner — Benjamin M Baldridge
(74) Attorney, Agent, or Firm — Hamilton, Brook, Smith & Reynolds, P.C.

(57) ABSTRACT

An ionization gauge includes an electron generator array that includes a microchannel plate that includes an electron generating portion of the microchannel plate comprising a source for generating seed electrons and an electron multiplier portion of the microchannel plate, responsive to the seed electrons generated by the electron generating portion, that multiplies the electrons. The ionization gauge includes an ionization volume in which the electrons impact a gaseous species, and a collector electrode for collecting ions formed by the impact between the electrons and gas species. The collector electrode can be surrounded by the anode, or the ionization gauge can be formed with multiple collector electrodes. The source of electrons can provide for a spontaneous emission of electrons, where the electrons are multiplied in a cascade.

32 Claims, 8 Drawing Sheets

(56) References Cited

U.S. PATENT DOCUMENTS

| | | | |
|---|---|---|---|
| 5,128,617 A * | 7/1992 | Bills | 324/459 |
| 5,132,586 A * | 7/1992 | Boulais et al. | 313/105 CM |
| 5,278,510 A * | 1/1994 | Baptist et al. | 324/460 |
| 5,278,586 A | 1/1994 | Yoneda et al. | |
| 5,866,901 A | 2/1999 | Penn et al. | |
| 6,203,568 B1 | 3/2001 | Lombardi et al. | |
| 6,239,549 B1 * | 5/2001 | Laprade | 313/533 |
| 6,515,482 B2 | 2/2003 | Kawasaki | |
| 6,534,923 B2 | 3/2003 | Espinosa | |
| 6,566,884 B2 * | 5/2003 | Rutherford et al. | 324/460 |
| 6,663,041 B2 | 12/2003 | Buschulte et al. | |
| 6,707,034 B1 * | 3/2004 | Yamaguchi et al. | 250/283 |
| 6,822,249 B2 | 11/2004 | Lee et al. | |
| 6,828,714 B2 * | 12/2004 | Downing et al. | 313/103 CM |
| 6,895,766 B2 | 5/2005 | Amundsen et al. | |
| 6,958,475 B1 | 10/2005 | Colby | |
| 7,030,619 B2 * | 4/2006 | Arnold et al. | 324/460 |
| 7,030,620 B2 * | 4/2006 | Correale | 324/460 |
| 7,038,223 B2 | 5/2006 | Starcher | |
| 7,049,823 B2 | 5/2006 | Correale | |
| 7,098,667 B2 | 8/2006 | Liu | |
| 7,129,708 B1 * | 10/2006 | Liu et al. | 324/464 |
| 7,183,701 B2 * | 2/2007 | Downing et al. | 313/103 R |
| 7,525,101 B2 | 4/2009 | Grodzins | |
| 7,544,046 B2 | 6/2009 | Beyer et al. | |
| 7,768,267 B2 * | 8/2010 | Knott et al. | 324/460 |
| 2003/0057953 A1 * | 3/2003 | Rutherford et al. | 324/460 |
| 2003/0146759 A1 | 8/2003 | Bashkirov et al. | |
| 2004/0017202 A1 | 1/2004 | Peacock et al. | |
| 2005/0030044 A1 | 2/2005 | Correale | |
| 2005/0184735 A1 * | 8/2005 | Arnold et al. | 324/464 |
| 2005/0218344 A1 * | 10/2005 | Starcher | 250/492.21 |
| 2005/0237066 A1 | 10/2005 | Liu et al. | |
| 2006/0012373 A1 | 1/2006 | Edelmann et al. | |
| 2006/0197537 A1 * | 9/2006 | Arnold et al. | 324/464 |
| 2006/0202701 A1 | 9/2006 | Knap et al. | |
| 2006/0261819 A1 | 11/2006 | Liu et al. | |
| 2007/0138388 A1 * | 6/2007 | Ward et al. | 250/288 |
| 2011/0062961 A1 * | 3/2011 | Brucker | 324/460 |
| 2011/0163754 A1 * | 7/2011 | Carmichael et al. | 324/460 |
| 2013/0106431 A1 * | 5/2013 | Liu et al. | 324/460 |

FOREIGN PATENT DOCUMENTS

| | | |
|---|---|---|
| GB | 2381652 A | 5/2003 |
| JP | 61-035325 | 2/1986 |
| JP | 61-145429 | 7/1986 |
| JP | 01-143928 | 6/1989 |
| JP | 03293533 A | 12/1991 |
| JP | 040006431 A | 1/1992 |
| JP | 07-181095 | 7/1995 |
| JP | 2000-329634 | 11/2000 |
| JP | 2001-166100 | 6/2001 |
| JP | 2001-357792 | 12/2001 |
| JP | 2005-062176 | 3/2005 |
| WO | WO 93/26032 | 12/1993 |

OTHER PUBLICATIONS

Notification Concerning Transmittal of International Preliminary Report on Patentability (Chapter 1 of the Patent Cooperation Treaty), PCT/US2008/013790, 8 pp., mailed Jul. 1, 2010.

First Official Letter, Chinese Patent Application No. 200880126701.2 date of mailing Aug. 11, 2011, with English Translation.

Decision of Rejection, Chinese Patent Application No. 200880126701.2 date of mailing Dec. 29, 2011, with English Translation.

\* cited by examiner

IONIZATION GAUGE HAVING ELECTRON MULTIPLIER COLD EMISSION SOURCE

RELATED APPLICATION

This application is the U.S. National Stage of International Application No. PCT/US2008/013790, filed 17 Dec. 2008, which designates the U.S., published in English, and claims the benefit of U.S. Provisional Application No. 61/008,185, filed 19 Dec. 2007. The entire teachings of the above application are incorporated hereby by reference.

BACKGROUND OF THE INVENTION

Bayard-Alpert (BA) ionization gauges are the most common non-magnetic means of measuring very low pressures and have been widely used worldwide since being disclosed in 1952 in U.S. Pat. No. 2,605,431, which is herein incorporated by reference in its entirety.

A typical ionization gauge includes an electron source, an anode, and an ion collector electrode. For the BA gauge, the electron source is located radially outside of an ionization space (anode volume) defined by the anode. The ion collector electrode is disposed within the anode volume. Electrons travel from the electron source toward and into the anode. In their travel, the electrons impact molecules and atoms of gas, constituting the atmosphere whose pressure is to be measured, and create ions.

The ions are attracted to the ion collector electrode by the electric field inside the anode. The pressure of the gas within the atmosphere can be calculated from ion and electron currents by the formula $P=(1/S)(I_{ion}/I_{electron})$, where S is a coefficient with the units of 1/Torr and is characteristic of a particular gauge geometry, and electrical parameters and pressure range. One well known problem in the art is that the hot cathode filament may react with the gaseous substances to be measured.

Ionization gauges with cold cathode electron emitters are also known, such as, for example, U.S. Pat. No. 5,278,510 to Baptist et al. (hereinafter "Baptist"), which is also incorporated by reference in its entirety. Baptist discloses an ionization gauge that includes a cold cathode instead of the hot cathode filament. Baptist's ionization gauge includes a number of cathode electrodes, which provide a bias voltage for a number of tipped micro-points (Spindt emitters). Electrons are emitted from the micro-points through field emission to ionize the gas, and thus measure pressure once the ions are collected, similar to the BA ionization gauge. However, after a short period of time, the tipped micro-points, which are bombarded by ionized gaseous material will erode. This degrades the emissivity, and leads to termination of electrons from the micro-tips. This renders the ionization gauge unable to measure pressure and causes the gauge to fail.

SUMMARY OF THE INVENTION

The operational lifetime of a typical BA ionization gauge is approximately ten years when the gauge is operated in benign environments. However, these same gauges and electron sources (filaments) can fail in minutes or hours when operated at too high a pressure or in gas types that degrade the emission characteristics of the electron source. Well known examples of such filament interactions, leading to decreased operational lifetime are due to chemical reactions with some gaseous environments, and can lead to degradation of the electron emission properties of the oxide coating on the filament. Degradation of the oxide coating dramatically reduces the number of electrons generated by the filament. Tungsten filaments also experience degradation of emission properties under these conditions, and additionally exposure to water vapor at too high a pressure results in the complete burnout of a tungsten filament. A reliable cold electron emitter would avoid these known problems. There is a need in the art for a cold electron emitter ionization gauge that will function without the drawbacks of the BA ionization gauge, without changing the chemical composition of the gas species in the chamber, and without degrading the gauge.

There is provided an ionization gauge that need not use a hot cathode filament, and includes an electron generator array including a microchannel plate that includes an electron generating portion of the microchannel plate comprising a source for generating seed electrons and an electron multiplier portion of the microchannel plate, responsive to the seed electrons generated by the electron generating portion, that multiplies the electrons. The microchannel plate can be treated to cause a spontaneous emission of seed electrons. The ionization gauge includes an ionization volume in which the electrons impact a gaseous species, and a collector electrode for collecting ions formed by the impact between the electrons and the gaseous species. The ionization volume can be defined by an anode which retains the electrons therein, and the source that generates the electrons can be outside of the anode. The collector electrode may be surrounded by the anode. The ionization gauge can include a second collector electrode to collect ions formed outside of the anode. The ionization volume can be defined by a volume between a plate shaped anode and a plate shaped collector electrode, and the source can be located between the plate shaped anode and the plate shaped collector electrode. The ionization gauge can be a cold electron source type ionization gauge that measures pressure by measuring current collected by the collector electrode. The ionization gauge can include an adjustor that controls an electron beam current from the electron generator array based on the number of electrons in the ionization volume, and an ammeter connected to an anode for controlling the electron beam current. Initial electrons may be provided to the electron multiplier by an intrachannel spontaneous field emission process, a field emitter array, a photocathode, or carbon nanotubes. The electron multiplier may use a microchannel plate that requires a high voltage differential between an input side, and an output side, where the high voltage differential value controls the electron emission current value. The microchannel plate can include an electron emitting material on the input face of the electron multiplier portion of the microchannel plate, wherein radiation produces seed electrons. The multiplier may include a microsphere plate, a single channel multiplier, a discrete dynode or multiple dynodes. Additionally, there are electron sources where both the seed electron generation and the electron multiplication are integrated to a single device.

In another embodiment, there is provided an ionization gauge that includes an anode structure including a cylindrical wire grid defining an ionization volume in which electrons impact a gaseous species, and a source that generates electrons that includes an electron seed device and an electron multiplier device that multiplies electrons from the electron seed device. The electron multiplier device can include a microchannel plate. The ionization gauge also includes a collector electrode that collects ions formed by the impact between the electrons and the gaseous species. One of the collector electrode and the source can be located inside the anode structure, and the other of the collector electrode and the source can be located outside the anode structure. Current collected by the collector electrode can form a pressure signal. The cylindrical wire grid can be configured as a plurality of wire circles coupled to at least one support strut. The source that generates electrons can be located outside the anode structure and the collector electrode can be located inside the anode structure. The ionization gauge can include a second collector electrode located outside the anode structure. Alternatively, the source that generates electrons can be located inside the anode structure and the collector electrode can be located outside the anode structure. In another embodiment, the ionization volume can be defined by a volume between a plate shaped anode and a plate shaped collector electrode, and the source can be located between the plate shaped anode and the plate shaped collector electrode.

In yet another embodiment, there is provided an ionization gauge that includes an anode structure including a cylindrical wire grid defining an ionization volume in which electrons impact a gaseous species, and an electron generator array including a microchannel plate that includes an electron generating portion of the microchannel plate comprising a source for generating seed electrons and an electron multiplier portion of the microchannel plate, responsive to the seed electrons generated by the electron generating portion, that multiplies the electrons. The ionization gauge also includes a collector electrode located inside of the anode structure, that collects ions formed by the impact between the electrons and the gaseous species. Current collected by the collector electrode can form a pressure signal. The cylindrical wire grid can be configured as a plurality of wire circles coupled to at least one support strut. The source that generates electrons can be located outside the anode structure and the collector electrode can be located inside the anode structure. The ionization gauge can include a second collector electrode located outside the anode structure. Alternatively, the source that generates electrons can be located inside the anode structure and the collector electrode can be located outside the anode structure.

In yet another embodiment, there is provided an ionization gauge that includes an electron generator array means for generating electrons and multiplying the generated electrons, an anode means comprising a cylindrical wire grid defining an ionization volume in which electrons impact a gaseous species, a collector electrode means for collecting ions formed by impact between electrons and the gaseous species, and means for forming a signal from the collected ions to determine pressure.

A method of measuring a gas pressure from a gaseous species is also provided. The method has the steps of producing electrons using an electron generator array including an electron generating portion of a microchannel plate, and multiplying electrons using an electron multiplier portion of the microchannel plate. The method also includes collecting ions that are formed from an impact between the electrons and the gas species, and forming a pressure signal from the collected ions. The method can include multiplying electrons by passing the electrons through a surface-treated microchannel plate. The method can further include producing the electrons between a plate shaped anode and a parallel plate shaped ion collector and collecting the ions on the parallel shaped ion collector.

Another method of measuring a gas pressure from a gaseous species has the steps of producing electrons using a source that includes an electron seed device, multiplying the electrons, collecting ions formed by impact between the electrons and the gaseous species using a collector electrode, and forming a pressure signal from the collected ions. One of the collector electrode and the source can be located inside an anode structure including a cylindrical wire grid defining an ionization volume in which electrons impact a gaseous species, and the other of the collector electrode and the source can be located outside the anode structure. In one embodiment, the source that generates electrons can be located outside the anode structure and the collector electrode can be located inside the anode structure. The method can include collecting ions outside of the anode structure using a second collector electrode located outside of the anode structure. Alternatively, the source that generates electrons can be located inside the anode structure and the collector electrode can be located outside the anode structure. Multiplying electrons can include passing the electrons through at least one surface-treated microchannel plate. Alternatively, multiplying electrons can include using at least one dynode.

According to yet another aspect of the present disclosure, there is provided a process that includes providing a substrate, evacuating a tool to perform processes on the substrate in the evacuated tool, measuring pressure, and conducting operations on the substrate in the evacuated tool to form a processed substrate. The method for measuring pressure includes providing an anode structure comprising a cylindrical wire grid defining an ionization volume in which electrons impact a gaseous species, a source, located outside of the anode structure, that generates electrons that includes an electron seed device and an electron multiplier device that multiplies electrons from the electron seed device, and a collector electrode located inside of the anode structure, that collects ions formed by the impact between the electrons and the gaseous species.

According to yet another aspect of the present disclosure, there is provided a process that includes providing a substrate, evacuating a tool to perform processes on the substrate in the evacuated tool, measuring pressure, and conducting operations on the substrate in the evacuated tool to form a processed substrate. The method for measuring pressure includes providing an electron generating array including a microchannel plate that includes an electron generating portion of the microchannel plate including a source for generating seed electrons and an electron multiplier portion of the microchannel plate, responsive to the seed electrons generated by the electron generating portion, that multiplies the electrons. The method also includes providing an ionization volume in which the electrons impact a gaseous species, and a collector electrode that collects ions formed by the impact between the electrons and the gaseous species.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

Figure 1A:
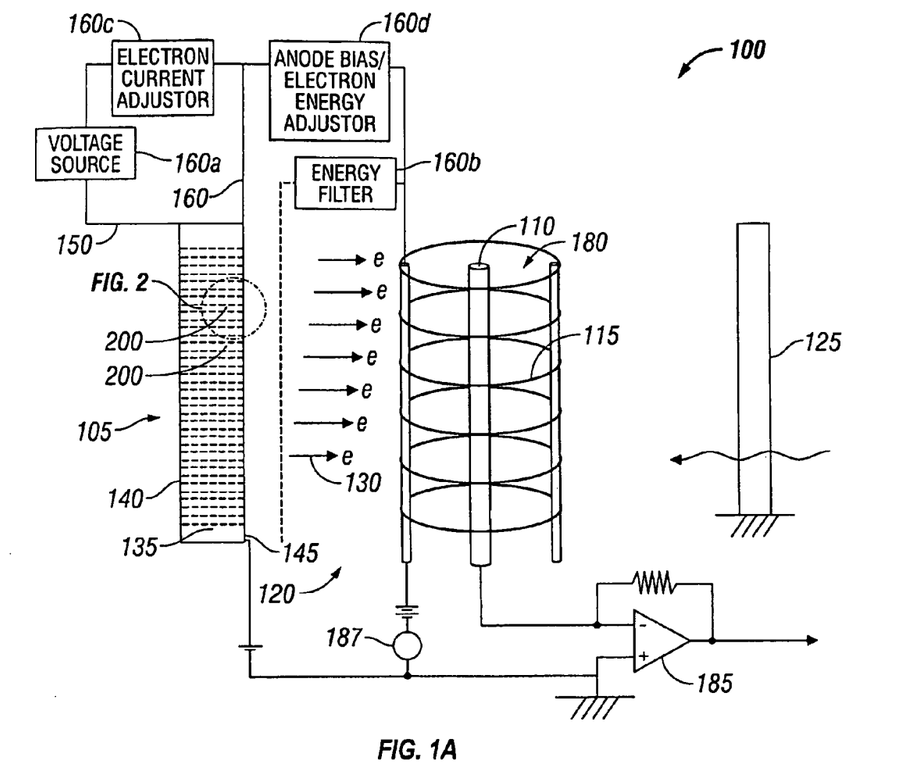
FIG. 1A is a schematic view of a generalized ionization gauge according to the present disclosure.

Generally, as shown in FIG. 1A, an ionization gauge 100 of the present disclosure includes an electron generator array 105, an ion collector electrode 110, and an anode 115. Although the ionization gauge 100 is shown with an anode 115, and collector electrode 110, these components are not needed in all embodiments of the invention as described below and various different ionization gauge configurations are possible. In one embodiment, the ionization gauge 100 is a non-Bayard-Alpert type gauge, or a cold electron emitter ionization gauge, and does not include any hot cathode filament as the electron source for the gauge 100. Instead, ionization gauge 100 is formed in a cold electron emitter gauge configuration and includes a source for generating seed electrons together with a source for multiplying the seed electrons collectively shown as reference numeral 105 as the electron generating array.

Figure 8:
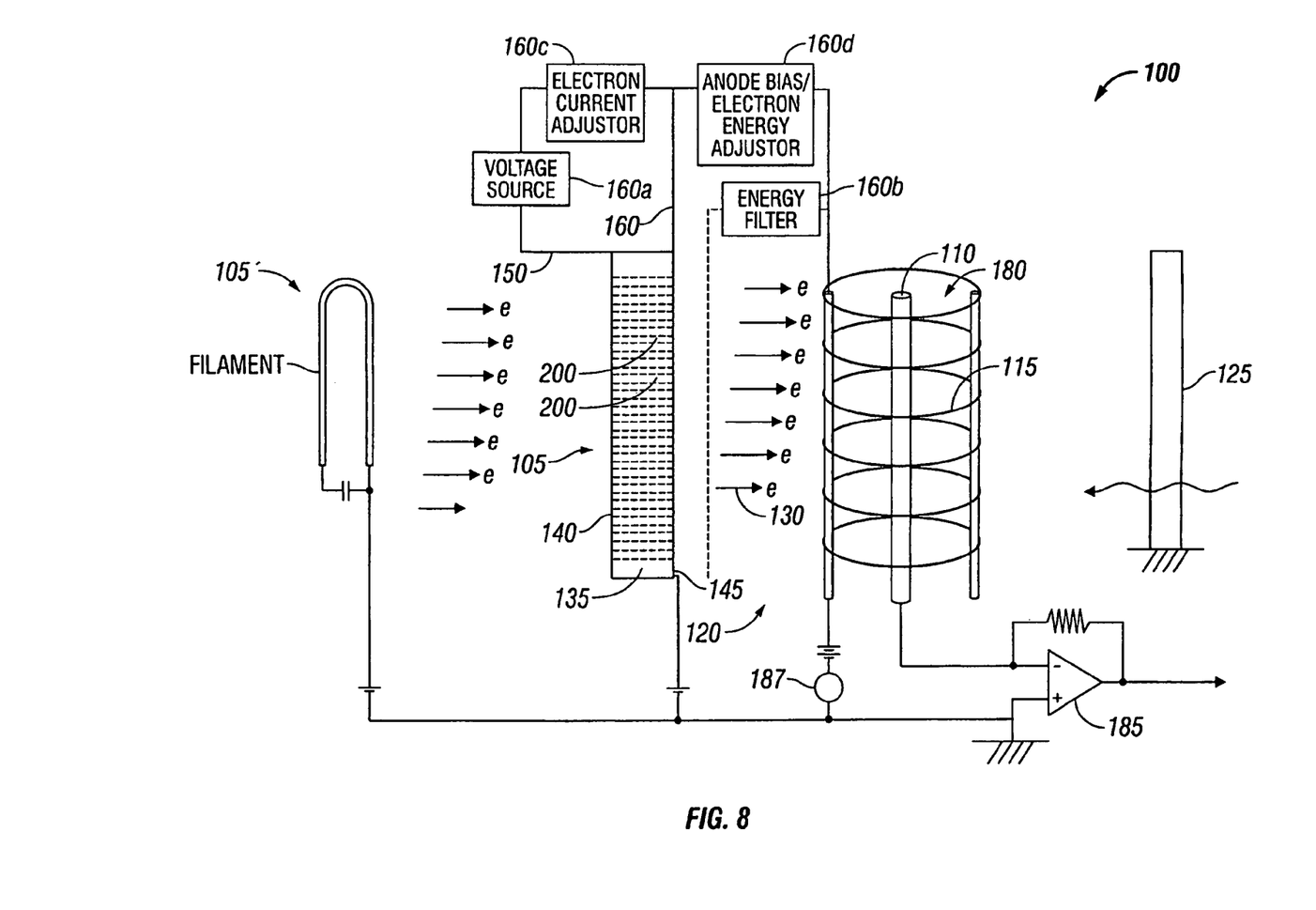
FIG. 8 shows an embodiment of an ionization gauge with both a cold electron emitter and a hot cathode filament.

Ionization gauge 100 may also include a plurality of cold electron emitters 105 as the seed electron source as described. Emitters 105 are generally located near the anode 115 in a manner similar to that shown in FIG. 1A, but at an additional azimuthal location around the cylindrical anode 115 that is shown. The electron source 105 may also be located adjacent to an end of the cylindrical anode 115 that is shown in FIG. 1A. Moreover, as a back-up for the cold electron emitter 105 as required for unforeseen environmental conditions that may be detrimental to the operation of the cold electron emitter 105, an additional conventional second hot cathode 105' (FIG. 8) may also be located in the gauge assembly 100 in a manner similar to that of the plurality of cold cathode emitters 105 described above. This will provide for future unknown gas environments not currently in practice. It will also provide added emission if needed for extremely low pressures where the ion current used for a pressure signal will be extremely small.

FIG. 1A shows a specific "nude type" ionization gauge 100 embodying the present invention. Although, a "nude type" ionization gauge 100 is shown, it should be understood that a "non-nude type" ionization gauge 100 can be employed using the principles of the present invention. The ionization gauge 100 may be housed in a tube (not shown), which is opened at one end to allow gaseous species to enter a measurement chamber 120 through a shield 125. Gaseous species can include gas molecules and atoms. The shield 125 and tube may form a shield volume, which can be differently sized depending on the application. It is also envisioned that an optional second ion collector (not shown) can also be added to the ionization gauge 100 for high pressure measurements of very short mean free paths. It is also envisioned in an alternative embodiment that the collector electrode 110 can be placed outside of the anode 115, while the source 105 can be placed inside the anode 115.

In operation, molecules and atoms of gas enter the measurement chamber 120 through the partially open shield 125. The cold electron emitter 105 operates generally at about 30 volts with respect to ground, and the anode 115 operates at about 180 volts with respect to ground, and a collector 110 operates near a ground potential. The shield 125 prevents potentials external to the shield 125 from disturbing the electric charge distribution within the measurement chamber 120. The shield 125 can be maintained at a reference potential. In one embodiment, the reference potential is ground potential.

The array or electron source 105 that emits an electron beam shown generally by reference numeral 130 is also located within a chamber 120. However, the electron seed source 105 can alternatively be located in a different chamber than the anode 115, and is shown in the same chamber 120 simply for illustration purposes, and the ionization gauge 100 is not limited to this particular configuration. The electrons 130 released from the source 105 are used in ionizing the gas molecules in the measurement chamber 120.

The electron generator array 105, not only includes a source for generating seed electrons, but it also includes a device for multiplying the seed electrons, and preferably can include an electron multiplier source, such as, for example, an EGA™ electron generating array from Burle Technologies Inc.®, or any other electron multiplier source, such as that described in U.S. Pat. No. 6,239,549 B1 to Laprade, which is herein incorporated by reference in its entirety. An electron generator array can include a microchannel plate that includes an electron generating portion of the microchannel plate comprising a source for generating seed electrons and an electron multiplier portion of the microchannel plate, responsive to the seed electrons generated by the electron generating portion, that multiplies the electrons. Other electron multiplier sources 105 are also envisioned such as, for example, those described in *Photomultiplier Tubes Basics and Applications*, Third Edition, Hamamatsu Photonics© K.K., 2006, which is herein incorporated by reference in its entirety. Preferably, array 105 can include any seed electron or current source as well as a source for spontaneous electron emission where the source can be excited by receiving particles or radiation. In response to receiving the particles or radiation, the source 105 further emits secondary electrons. These secondary electrons are then multiplied in a cascade. These electrons later ionize a gaseous species, and the ions are collected to measure pressure. Array 105 may also, alternatively, include an electron multiplier, such as, for example, a micro-sphere or microchannel plate, which are described in U.S. Pat. No. 6,828,714 to Downing et al., which is herein incorporated by reference in its entirety. Microsphere plates can include a glass plate formed of microscopic glass spheres that have semiconductive and electron emissive surfaces. The spheres are packed and bonded together by, for example, compression and sintering. As incident particles, such as, for example, electrons, ions, or photons, collide against the surfaces of the spheres to form secondary electrons, a cascade of electrons can be formed as the secondary electrons accelerate through the interstices defined by the spheres and collide against the surfaces of other spheres. Microchannel plates may be stacked in chevron (series) configurations to provide enhanced gain while preventing ion feedback. Microchannel plates may also be stacked in parallel (i.e. side-by-side) configurations designed to provide additional emission, emitter redundancy and improved emission flux symmetry around the anode. The array 105 may also include a multiplier with a number of interconnected fibers such as, for example, U.S. Pat. No. 7,183,701 to Downing et al., which is also herein incorporated by reference in its entirety. It should be appreciated that the electron source 105 may include two devices with one for generating seed electrons, which are multiplied by a second device, or a single device 105 that both generates seed electrons, and then multiplies the seed electrons in a cascade. Various configurations are possible and within the scope of the present disclosure, and the present disclosure is not limited to any specific configuration.

Figure 1B:
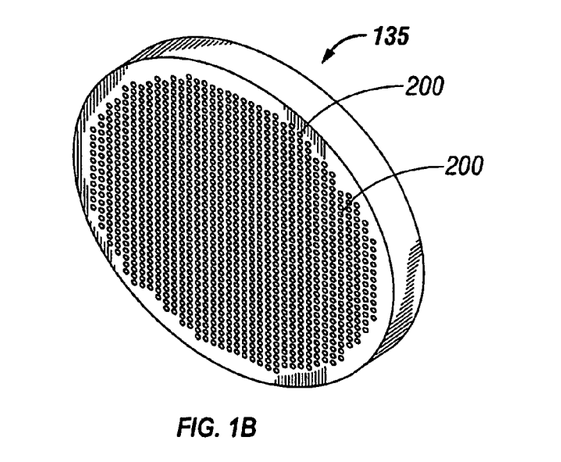
FIG. 1B shows a surface-treated microchannel plate of FIG. 1A having a number of pores.

As shown in FIG. 1A, the source 105 includes a surface-treated microchannel plate 135 having a number of pores 200, shown in a side view in FIG. 1A. The source 105 provides a surface for the spontaneous emission of electrons, which is used as an electron source for the cold cathode ionization gauge 100. The microchannel plate 135 includes an input face 140, and an output face 145, and a series of fused tubes, which are preferably glass tubes, and which form a number of pores 200 (FIG. 2) in a rigid structure. Overall, the plate 135 generally has a disk shape as shown in FIG. 1B that forms a number of tubes or pores 200. A voltage source 160a connects across plate 135, which multiplies the electrons in a cascade. The electron beam current which then exits the output face 145 can be adjusted by an electron current adjustor 160c which adjusts the voltage source 160a. The electron beam current is measured by the ammeter 187. This measured current information from the ammeter 187 is provided to the electron current adjustor 160c which then controls the electron beam current. The ammeter 187 measures an electron current generated in the grid 115 from electrons that arrive at the grid 115. This measured current represents the number of electrons being provided to the ionization volume from the source 105. The measured current information from the ammeter 187 is provided to components of the gauge 100 which uses the current information as feedback to control the source 105.

Figure 2:
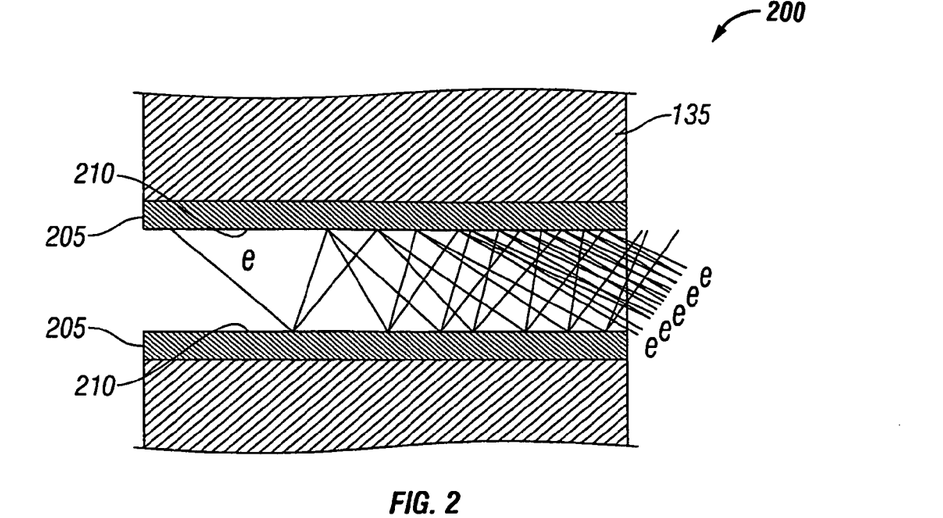
FIG. 2 is an enlarged view of a pore of the surface-treated microchannel plate of FIG. 1A with the pore including a material for multiplying received electrons.

When another initial electron source is supplied inside plate 135, then seed electrons are released to the pores 200 as shown in FIG. 2. The electrons will then contact the lateral sides of the pore and will multiply.

Turning again to FIG. 1A, the electron source 105 also has an energy filter to select the electrons along path 130, and direct them to the anode 115. The source 105 also includes an anode bias/energy adjustor 160d that is connected to the anode 115. An energy filter 160b is also provided to filter the electrons 130. Various initial electron source configurations are possible and within the scope of the present disclosure, and the present invention is not limited to any such initial source.

Once the voltage between the input face 140 and the output face 145 is supplied, a wide and instantaneous beam of electrons as shown by reference number 130 is discharged along a path. Electrons 130 are directed into the measurement chamber 120 and to the anode 110. Preferably, the beam of electrons 130 ionizes the gaseous species in the chamber 120 after a number of passes. In another alternative embodiment, the source 105 can include a metal oxide micro-size gap device, instead of the surface modified microchannel plate 135.

Other electron multiplying elements can be used in connection with the present disclosure, and the present gauge is not limited to any specific multiplier for source 105. The electron generator array elements that form the source 105 can be a single channel electron multiplier (FIG. 3), or may have various other electron multiplying configurations as discussed herein. The source for generating and multiplying electrons 105, in one embodiment, includes the surface treated microchannel plate 135 being subjected to an acid leaching after the plate 135 is formed, but before a hydrogen reduction step, as discussed in U.S. Pat. No. 6,239,549 B1 to Laprade. Spontaneous electron emission can be obtained from the microchannel plate with any acid leaching process, such as, for example, treatment with hydrochloric, acetic, nitric, or sulfuric acid solution of more than about 1% by volume for an exposure time exceeding about one minute, at a temperature above about 20° C.

Turning now to FIG. 2, there is shown a close-up view of another alternative element of the cold electron source ionization gauge 100, which includes an electron multiplying source 105 for generating electrons. In FIG. 2, a close-up view of a pore 200 of the modified microchannel plate 135 of the electron multiplier 105 is shown. Plate 135 of FIG. 1A can include a number of pores 200, and the pores 200 roughly each have a size of about 5 microns for electron emission to ionize gaseous material.

The microchannel plate 135 preferably can include a photocathode to provide the initial seed electrons. In one embodiment, when a photocathode at the entrance of pore 200 is struck by light, electrons are injected into the pore 200 and electrons in a beam 130 are emitted from the exit of pore 200.

In this embodiment, the pore 200 of the microchannel plate 135 of FIG. 1A includes a coating 205 on a first surface 210 of the pore 200. The coating 205 is preferably an alkali-containing compound, which serves to lower a work function of the surface, and is configured for electron emission. Other coatings 205 are also envisioned including Ag—O—Cs, also called S-1, antimony-cesium, a bi-alkali, a high temperature bi-alkali or low noise bi-alkali, gallium (III) arsenide, a multi-alkali, indium gallium arsenide, a cesium telluride, or cesium iodine. The present gauge is not limited to any specific coating 205, and may multiply electrons without a coating 205.

Figure 3:
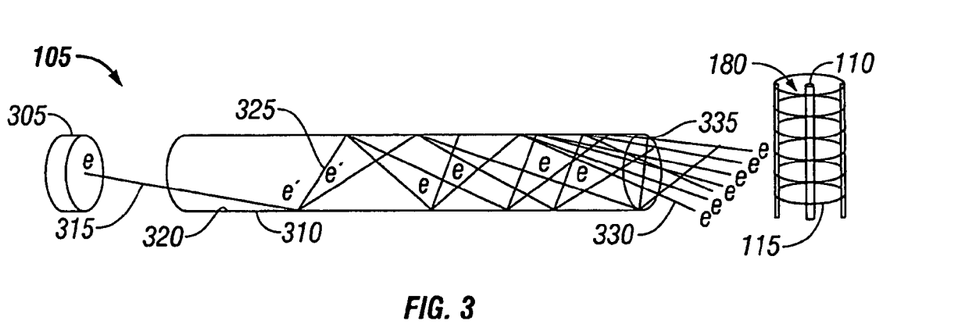
FIG. 3 shows a schematic view of another embodiment of an element as the source for generating and multiplying electrons with a single channel configuration according to the present disclosure.

Turning now to FIG. 3, other elements of the array 105 are envisioned instead of those described in FIG. 1A. Other elements can be used to generate and multiply the electrons including a single channel electron multiplier, a discrete dynode electron multiplier, or any other electron multiplier known in the art. Moreover, multiple microchannel plates may be used as the source 105 with the multiple microchannel plates arranged in a Burle Technologies® Inc's "Chevron Configuration"™, or in a Burle Technologies® Inc's "Z-Configuration"™ as described in U.S. Pat. No. 6,239,549 B1 to Laprade.

Turning to FIG. 3, there is shown an alternative embodiment for an element of the array 105 shown in FIG. 1A. FIG. 3 shows a source of electrons 305, which can be any electron source known in the art, such as a current source, a cathode, or a photocathode. Source 305 can be connected to a single channel electron multiplier tube 310. Other sources 305 can include a field emission source, a field emitter array, an energetic electromagnetic source, carbon tubes, Al:ZnO whiskers and coated carbon velvet emitters. An electron 315, which is released from, for example, an electron source (or cathode 305) is directed to a location in the tube 310. The electron 315 hits a wall 320 of the electron multiplier tube 310. This contact releases more electrons 325, and creates a cascading effect, so that a single electron 315 gives rise to a plurality of electrons 330 emerging at a distal end 335 of the single channel electron multiplier tube 310. The multiple electrons 330 are released to the measurement chamber 120 of FIG. 1A and collide with the gaseous substance. Ions are then collected by a collector electrode 110.

Figure 4:
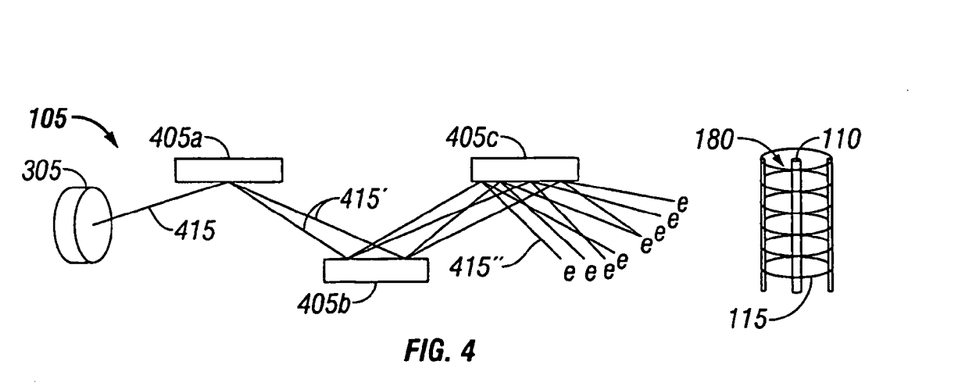
FIG. 4 shows yet another embodiment of an element as the source for generating and multiplying electrons having a cathode, and a plurality of dynodes.

Turning now to FIG. 4, there is shown another alternative embodiment of an element of the array 105 shown in FIG. 1A.

Here, the element of the array 105 for generating electrons includes an initial electron source 305 and a source for multiplying the electrons that includes at least one dynode 405a. Source 305 can be a field emission source, a cathode, or a photocathode, or a different electron source than discussed above with regard to FIG. 3. In this embodiment, the array 105 also further includes a plurality of discrete dynodes 405a, 405b, and 405c instead of multiple pores 200 shown in FIG. 1A.

A dynode 405a is one of a series of electrodes which may be disposed within a photomultiplier tube (not shown). Each dynode 405c, 405b, 405a is more positively charged than its predecessor. A secondary emission occurs at the surface of each dynode 405b, 405c, which releases electrons in a cascading manner. Such an arrangement is able to amplify the applied current emitted by the initial electron source 305, such as, for example, current source, a photocathode, or cathode by typically about one million. Accordingly, the electrons 415 emitted from the initial cathode 305, or electron source are accelerated toward the first dynode 405a, which is maintained 90 to 100 volts positive with respect to the voltage of the cathode 305. Each accelerated seed photoelectron that strikes the first dynode surface 405a produces many more electrons. These are then accelerated, or otherwise directed to the second dynode 405b, which is held 90 to 100 volts more positive than the first dynode 405a. Each accelerated electron that strikes the second dynode surface 405b produces many more electrons, that are then accelerated, or otherwise directed to the third dynode 405c, which is held 90 to 100 volts more positive than the second dynode 405b.

This process, of course, can be repeated for more than three dynodes, and is not limited to any specific number of dynodes 405a through 405c. This process repeats at each of the dynodes 405a, 405b, 405c, and a range of electrons 415" may include a large number, such as, for example, about $1\times10^5$ to $1\times10^7$ electrons 415" being produced for each incident electron, which provides for a suitable amount of electrons 415" to ionize the desired gas, and, thus, measure pressure in the ionization gauge 100 of FIG. 1A. The foregoing numbers are simply for illustration purposes and the present gauge is not limited to any such quantities.

As shown, a single seed electron 415 emitted from the cathode 305, or the electron current source, gives rise to a plurality of electrons 415', 415". Various numbers of dynodes can be used and the present ionization gauge 100 is not intended to be limited to any specific number of dynodes 405a, 405b, and 405c, and any number is within the scope of the present disclosure, and may depend on the gaseous substance.

Turning again to FIG. 1A, it should be appreciated that the electrons 130 must have their energy controlled to a desired level to allow for ionization to occur after the electrons 130 have been transmitted into the measurement chamber 120. Ionization occurs over an energy spread both higher and lower than the nominal design energy; see Section 5.7 on ionization gauges in *Scientific Foundations of Vacuum Technique* by Saul Dushman, 1962, which is herein incorporated by reference in its entirety. Ion formation typically occurs at an electron energy around 150 electron volts for nitrogen. Various ion formation configurations are possible and within the scope of the present disclosure.

The anode structure 115 comprises a cylindrical wire grid that defines an ionization volume 180, which is charged to, for example, a positive 180 volts with reference to ground. The anode structure grid 115 can be made of a wire mesh or a plurality of wire circles coupled to at least one support strut. The design of the anode structure grid 115 allows the electrons 130 to enter the anode grid 115. Most electrons 130 likely do not strike the anode grid 115. Instead, the electrons 130 pass into the anode grid 115 and are controlled to stay in the ionization anode volume 180. Here, the electrons 130 create ions through electron impact ionization.

The ions, once created by electron impact ionization, tend to stay within the anode grid 115. The ions formed within the anode volume 180 (of the anode grid 115) are directed by the electric field produced by the potential difference between (a) the anode grid 115 at a potential that is positive with respect to ground, and (b) the collector electrode 110, which is at a potential which is near ground potential (i.e., negative relative to the anode grid 115 potential). This electric field directs the ions to the collector electrode 110 where they are collected to provide the ion current, which is amplified by an amplifier 185 (FIG. 1A), and which is used to determine the pressure of the gas.

Figure 5:
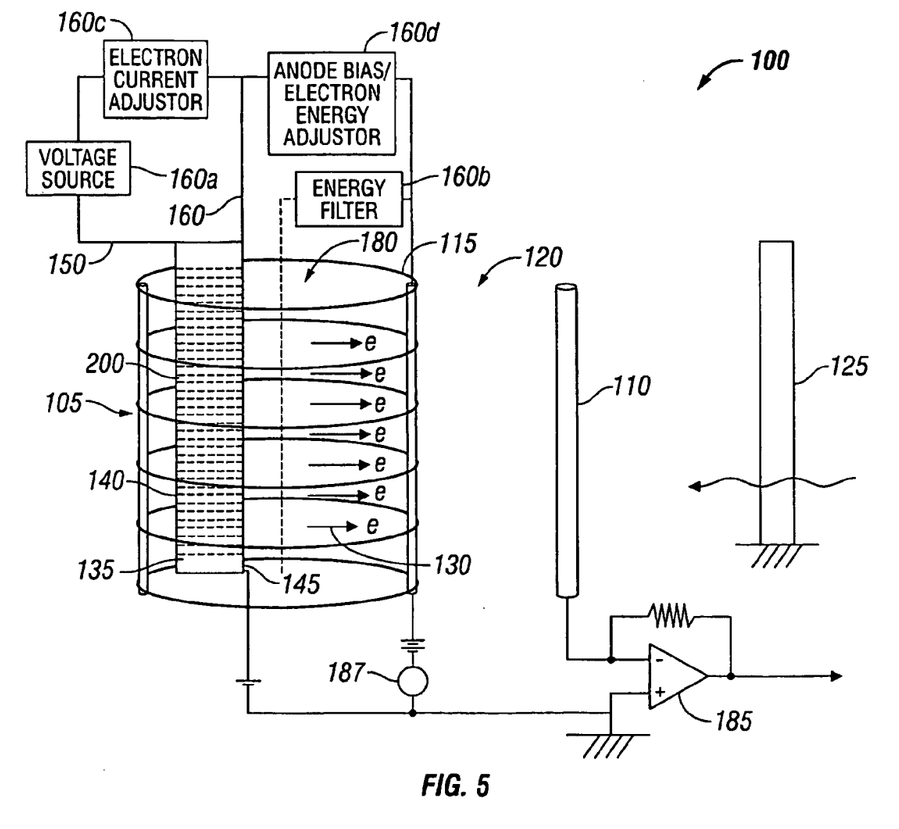
FIG. 5 shows an embodiment as a triode ionization gauge.

In another preferred embodiment, the source for generating seed electrons and multiplying the seed electrons 105 can be placed in the anode 115, while the collector electrode 110 is placed outside the anode 115 (FIG. 5, showing the source 105 in a side view). In a further embodiment shown in FIG. 5, the ionization gauge 100 may be configured as a triode gauge with the electron generating array 105 being located inside the anode 115 while the collector electrode 110 is located outside the anode 115. Various ionization gauge configurations are possible, and the present disclosure is not limited to any particular configuration. In some embodiments, higher pressures can be measured using a second ion collector 110b (FIG. 6) which is in a different location relative to electrode 110 for the capture of ions formed closer to the source 105 either inside or outside the anode 115.

Figure 6:
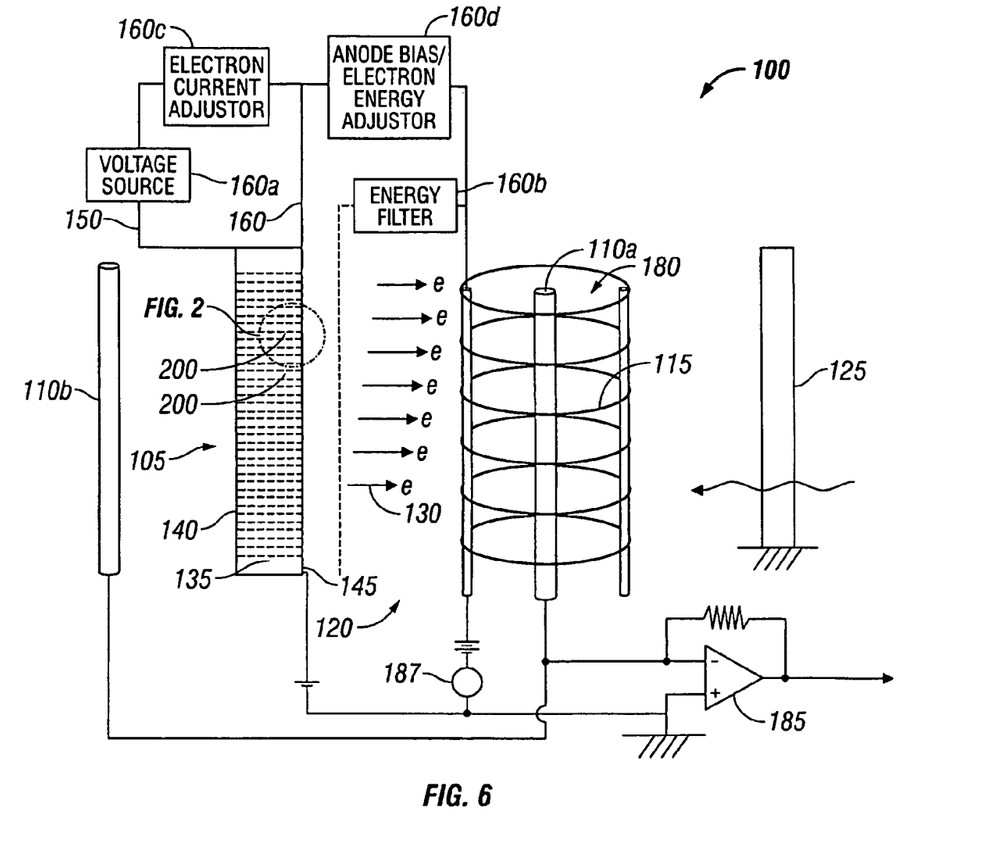
FIGS. 6 and 7 shows embodiments with multiple ion collector electrodes.

In another embodiment of the present disclosure, the gauge 100 may be configured to include two ion collectors 110a and 110b with a first ion collector being located in the anode 115 and a second ion collector 110b being located outside the anode 115. In this embodiment, the source for generating seed electrons and multiplying the seed electrons 105, shown in a side view in FIG. 6, can be placed outside the anode 115. The second ion collector 110b is configured to collect ions formed outside the anode 115 at high pressure, as shown in FIG. 6.

Figure 7:
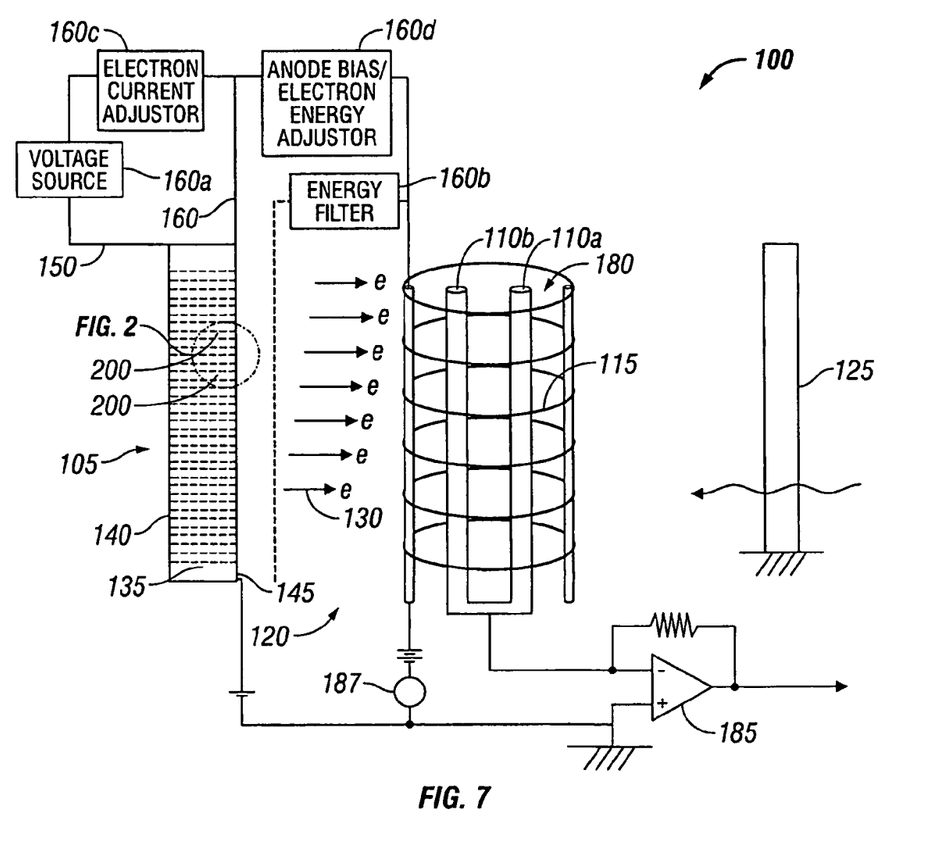

Here, the ionization gauge 100 includes a second ion collector electrode 110b in addition to the electrode 110a. Second ion collector electrode 110b is positioned outside of the grid 115 to assist with ion collection. The ions, once created by electron impact ionization, tend to stay within the grid 115. This collector current is then amplified by the amplifier 185 and provided to an electrometer. The electrometer provides an indication of the strength of the collector current, which is calibrated in units of pressure. Additionally, both collector electrodes 110a, 110b may be, alternatively, positioned in the anode 115 as shown in FIG. 7. It should be appreciated that a pressure signal (current) from both ion collector electrodes 110a, 110b will be added together to determine the pressure.

In one embodiment, a controller (not shown) may select which signal from collector electrode 110a or collector electrode 110b to use to determine the pressure. For example, at relatively low pressures, the pressure signal (current) is predominantly measured from a collector electrode 110a located inside anode 115, and at relatively higher pressures, the current is predominantly selected from the outside collector 110b.

Figure 9:
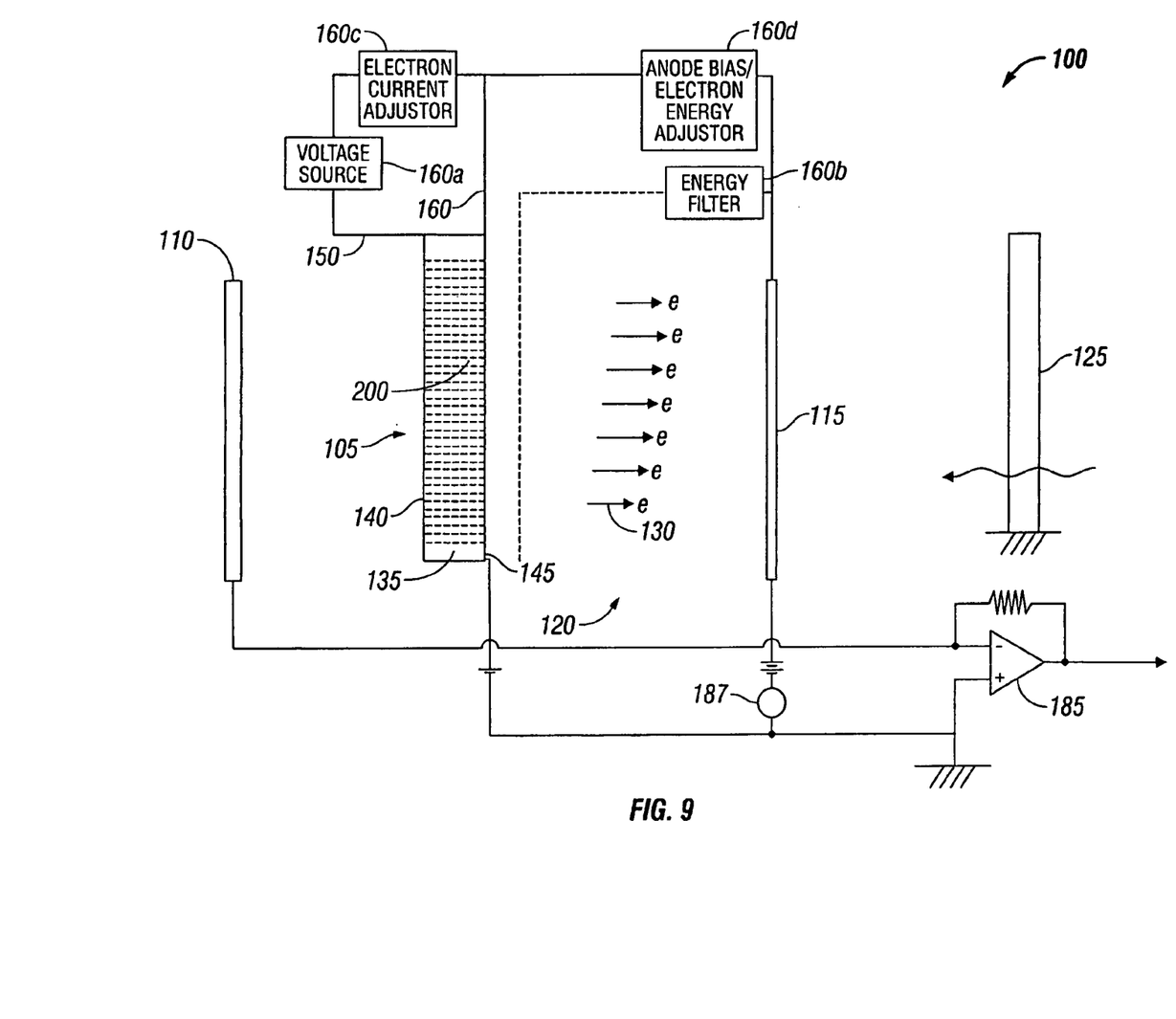
FIG. 9 shows another embodiment of an ionization gauge with an electron multiplier in a Schultz-Phelps geometry where the anode is a flat plate, the ion collector is another flat plate parallel to the anode and the electron source is between the two plates.

In another embodiment shown in FIG. 9, gauge 100 may be configured in a Schultz-Phelps geometry with the anode 115 being arranged as a flat plate, shown as a side view, the ion collector 110 as a parallel flat plate, shown as a side view, and the electron source 105, also shown as a side view, positioned between those two plates 110, 115.

It should be appreciated that using the source for generating and multiplying electrons 105 results in a fast turn on time, without the need to allow a conventional BA ionization gauge to warm up (such as when using a hot cathode filament as the source of seed electrons for the BA ionization gauge). Other advantages include that the gauge 100 may be configured to use external and internal DC and AC magnetic and electric fields to enhance electron trajectory lengths, and to affect a gain of the electron multiplier source 105, and to otherwise direct the beam of electrons 130 to the anode grid 115. The present ionization gauge 100 can use an amplifier 185 (FIG. 1A) to amplify current, and the source for generating and multiplying electrons 105 can be configured to face toward, or face away from the anode 115. This arrangement (facing away from anode 115) may eliminate line of sight contamination from vacuum processes, and can also narrow the energy bandwidth of the electrons 130. The ionization gauge 100 may also be mounted to focus the beam of electrons 130. Various mounting configurations are possible and within the scope of the present disclosure.

Figure 10:
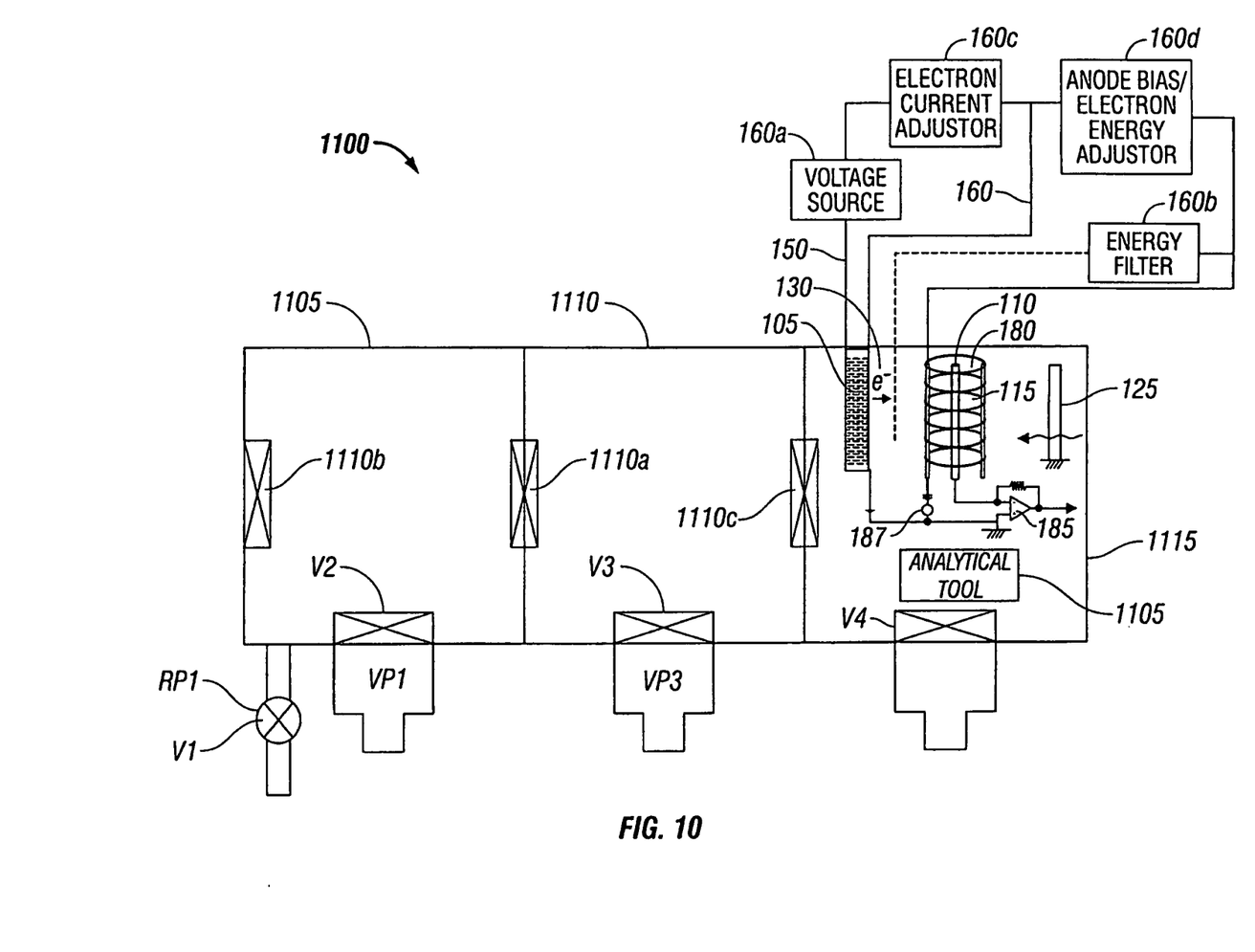
FIG. 10 shows an ionization gauge in a process module with an analytical tool.

Turning now to FIG. 10, the ionization gauge 100 preferably can be used with a cluster tool 1100 or another multi-chamber tool for processing operations. In one embodiment, the cluster tool 1100 may include a load lock chamber 1105 connected to a transfer chamber 1110 by a valve 1110a. The load lock chamber 1105 is sealed from ambient conditions by a valve 1110b. Both a single chamber and multi-chamber cluster tools 1100 are envisioned, and the ionization gauge 100 can be used in either a single chamber or a multi-chamber tool configuration. It should be appreciated that the ionization gauge 100 is not limited for use with a vacuum chamber, and can be used in any manufacturing chamber known in the art.

The cluster tool 1100 may also include a process module 1115. Process module 1115 is also connected to the transfer chamber 1110 by a valve 1110c. The tool 1100 may includes multiple process modules 1115 and multiple load lock chambers 1105, and the configuration shown is not limiting. The load lock chamber 1105 may include a rough pump RP1, which also is connected to the load lock chamber 1105 by a valve $V_1$. Each of the load lock chamber 1105, the transfer chamber 1110, and the process module 1115 may include at least one vacuum pump $Vp_1$, $Vp_2$, and $Vp_3$. The vacuum pump may be a cryogenic vacuum pump, or another pump, such as a turbo pump or water vapor pump. Various pumping configurations are possible and within the scope of the present disclosure.

Preferably, a wafer (not shown) may be introduced into the load lock chamber 1105, and pumped to vacuum conditions using the rough pump $Rp_1$ and the vacuum pump $Vp_1$. Using a wafer manipulating robot (not shown), the wafer can be manipulated to the transfer chamber 1110 through the valve 1110a, and then the wafer can be placed in the process module 1115 through the valve 110c for various deposition operations. In one embodiment, the ionization gauge 100 may be placed in one of the chambers 1105, 1110, or 1115 of the cluster tool 1100. For illustration purposes, the ionization gauge 100 is shown in the process module 1115, but is not limited to any specific chamber or location, and can be placed outside of the chamber or tool 1100.

The ionization gauge 100 preferably can measure pressure both base pressure (high vacuum) and higher processing pressures (mostly in the mTorr range), however this is not limiting and various operational parameters for measurement are possible and within the scope of the present disclosure. The ionization gauge 100 can be used to measure pressure in the manufacture of flat panel displays, magnetic media operations, solar cells, optical coating operations, semiconductor manufacturing operations, and other manufacturing process operations. Such processes may include physical vapor deposition, plasma vapor deposition (PVD), chemical vapor deposition (CVD), atomic layer deposition (ALD), plasma etch operations, implantation operations, oxidation/diffusion, forming of nitrides, vacuum lithography, dry strip operations, epitaxy operations (EPI), rapid thermal processing (RTP) operations, extreme ultraviolet lithography operations, and others. Preferably, the ionization gauge 100 may also be operable with one or more analytical tools, such as, for example, a microscope or a mass spectrometer. Mass spectrometers may include gas chromatograph instruments (GC), liquid chromatograph instruments (LC), ion trap instruments, magnetic sector spectrometers instruments, double-focusing instruments, time-of-flight instruments (TOF), rotating field instruments, ion mobility instruments, linear quadrupole instruments, and others.

Surface analytical instruments 1105 that can be used in connected with the ionization gauge 100, and with the cluster tool 1100 (or without the cluster tool 1100) may also include scanning electron microscopes, energy dispersive X-ray spectroscopy instruments (EOS/XPS), scanning auger microanalysis instruments (Auger/SAM), glow discharge mass spectroscopy instruments (GDMS), electron spectroscopy for chemical analysis instruments (ESCA), atomic force microscopy/scanning probe microscopy instruments (AFM/SPM), Fourier transform infrared spectroscopy instruments (FTIR), wavelength dispersive X-ray spectroscopy instruments (WDS), inductively coupled plasma mass spectroscopy instruments (ICPMS), x-ray fluorescence instruments (XRF), neutron activation analysis instruments (NAA), metrology instruments, and others. It should be appreciated that this listing is not exhaustive and the gauge 100 may be used with other instruments not listed.

While this invention has been particularly shown and described with references to preferred embodiments thereof, it will be understood by those skilled in the art that various changes in form and details may be made therein without departing from the scope of the invention encompassed by the appended claims.

What is claimed is:

1. An ionization gauge, comprising:
an electron generator array including a microchannel plate including:
an electron generating portion of the microchannel plate comprising a source for generating seed electrons, and an electron multiplier portion of the microchannel plate, responsive to the seed electrons generated by the electron generating portion, that multiplies the electrons;
an ionization volume in which the electrons impact a gaseous species;
an adjustor that controls an electron beam current from the electron generator array based on feedback of number of electrons in the ionization volume;
an energy filter that controls energy of the electrons in the ionization volume;
and a collector electrode that collects ions formed by the impact between the electrons and the gaseous species.

2. The ionization gauge of claim 1, wherein the ionization volume is defined by an anode which retains the electrons therein, and wherein the source that generates electrons is outside of the anode, and wherein the anode surrounds the collector electrode.

3. The ionization gauge of claim 2, further comprising a second collector electrode to collect ions formed outside of the anode.

4. The ionization gauge of claim 2, further comprising an ammeter connected to the anode for measuring the number of electrons in the ionization volume and controlling the electron beam current.

5. The ionization gauge of claim 1, wherein current collected by the collector electrode forms a pressure signal.

6. The ionization gauge of claim 5, wherein the ionization volume is defined by a volume between a plate shaped anode and a plate shaped collector electrode, and wherein the source is located between the plate shaped anode and the plate shaped collector electrode.

7. The ionization gauge of claim 1, wherein the microchannel plate includes an input face and an output face, and wherein voltage is applied between the input face and the output face.

8. The ionization gauge of claim 7, wherein the microchannel plate is treated to cause a spontaneous emission of seed electrons.

9. The ionization gauge of claim 8, wherein an electron emitting material is on the input face of the electron multiplier portion of the microchannel plate, and wherein radiation produces seed electrons.

10. An ionization gauge comprising:
an anode structure comprising a cylindrical wire grid defining an ionization volume in which electrons impact a gaseous species;
a source that generates electrons that includes an electron seed device and an electron multiplier device that multiplies electrons from the electron seed device;
an adjustor that controls an electron beam current from the electron generator array based on feedback of number of electrons in the ionization volume;
an energy filter that controls energy of the electrons in the ionization volume;
and a collector electrode that collects ions formed by the impact between the electrons and the gaseous species, one of the collector electrode and the source being located inside the anode structure, and the other of the collector electrode and the source being located outside the anode structure.

11. The ionization gauge of claim 10, wherein the cylindrical wire grid is configured as a plurality of wire circles coupled to at least one support strut.

12. The ionization gauge of claim 10, wherein the source that generates electrons is located outside the anode structure and the collector electrode is located inside the anode structure.

13. The ionization gauge of claim 12, further including a second collector electrode located outside the anode structure.

14. The ionization gauge of claim 10, wherein the source that generates electrons is located inside the anode structure and the collector electrode is located outside the anode structure.

15. The ionization gauge of claim 10, wherein current collected by the collector electrode forms a pressure signal.

16. The ionization gauge of claim 10, wherein the electron multiplier device that multiplies electrons includes a microchannel plate.

17. An ionization gauge comprising:
an anode structure comprising a cylindrical wire grid defining an ionization volume in which electrons impact a gaseous species;
an electron generator array including a microchannel plate including: an electron generating portion of the microchannel plate comprising a source for generating seed electrons, and an electron multiplier portion of the microchannel plate responsive to the seed electrons generated by the electron generating portion, that multiplies the electrons;
an adjustor that controls an electron beam current from the electron generator array based on feedback of number of electrons in the ionization volume;
an energy filter that controls energy of the electrons in the ionization volume;
and a collector electrode located inside of the anode structure, that collects ions formed by the impact between the electrons and the gaseous species.

18. The ionization gauge of claim 17, wherein the cylindrical wire grid is configured as a plurality of wire circles coupled to at least one support strut.

19. The ionization gauge of claim 17, wherein the source that generates electrons is located outside the anode structure and the collector electrode is located inside the anode structure.

20. The ionization gauge of claim 19, further including a second collector electrode located outside the anode structure.

21. The ionization gauge of claim 17, wherein the source that generates electrons is located inside the anode structure and the collector electrode is located outside the anode structure.

22. The ionization gauge of claim 17, wherein current collected by the collector electrode forms a pressure signal.

23. An ionization gauge, comprising:
an electron generator array means for generating electrons and multiplying the generated electrons;
an anode means comprising a cylindrical wire grid defining an ionization volume in which electrons impact a gaseous species;
an adjustor means for controlling an electron beam current from the electron generator array based on feedback of number of electrons in the ionization volume;
an energy filter means for controlling energy of the electrons in the ionization volume;
a collector electrode means for collecting ions formed by impact between electrons and the gaseous species;
and means for forming a signal from the collected ions to determine pressure.

24. A method of measuring a gas pressure from a gaseous species, comprising the steps of:
producing electrons using an electron generator array including an electron generating portion of a microchannel plate;
multiplying electrons using an electron multiplier portion of the microchannel plate;
adjusting an electron beam current from the electron generator array based on feedback of number of electrons in an ionization volume;
filtering energy of the electrons in the ionization volume;
collecting ions formed by impact between the electrons and the gaseous species using a collector electrode;
and forming a pressure signal from the collected ions.

25. The method of claim 24, further comprising producing the electrons between a plate shaped anode and a parallel plate shaped ion collector and collecting the ions on the parallel plate shaped ion collector.

26. The method of claim 24, further comprising multiplying electrons by passing the electrons through a surface-treated microchannel plate.

27. A method of measuring a gas pressure from a gaseous species, comprising the steps of:
producing electrons using a source that includes an electron seed device; multiplying the electrons;
collecting ions formed by impact between the electrons and the gaseous species using a collector electrode, one of the collector electrode and the source being located inside an anode structure comprising a cylindrical wire grid defining an ionization volume in which electrons impact a gaseous species, and the other of the collector electrode and the source being located outside the anode structure;
adjusting an electron beam current from the electron generator array based on feedback of number of electrons in the ionization volume;
filtering energy of the electrons in the ionization volume; and forming a pressure signal from the collected ions.

28. The method of claim 27, wherein the source that generates electrons is located outside the anode structure and the collector electrode is located inside the anode structure.

29. The method of claim 27, wherein the source that generates electrons is located inside the anode structure and the collector electrode is located outside the anode structure.

30. The method of claim 27, further comprising multiplying electrons by passing the electrons through at least one surface-treated microchannel plate.

31. The method of claim 27, further comprising multiplying electrons using at least one dynode.

32. The method of claim 27, further comprising collecting ions outside of the anode structure using a second collector electrode located outside of the anode structure.

* * * * *

UNITED STATES PATENT AND TRADEMARK OFFICE
CERTIFICATE OF CORRECTION

PATENT NO. : 8,686,733 B2  Page 1 of 1
APPLICATION NO. : 12/808983
DATED : April 1, 2014
INVENTOR(S) : Gerardo A. Brucker It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 826 days.

Signed and Sealed this

Twenty-ninth Day of September, 2015

Michelle K. Lee
*Director of the United States Patent and Trademark Office*